US012343267B2

(12) United States Patent
Dun et al.

(10) Patent No.: US 12,343,267 B2
(45) Date of Patent: *Jul. 1, 2025

(54) ORTHOPAEDIC SURGICAL INSTRUMENT FOR TOTAL HIP ARTHROPLASTY AND ASSOCIATED ORTHOPAEDIC SURGICAL METHOD OF USE (71) Applicant: DEPUY SYNTHES PRODUCTS, INC., Raynham, MA (US)

(72) Inventors: Shouchen Dun, Fort Wayne, IN (US); Stephen W. Swope, North Webster, IN (US); Dustin R. Whitaker, Akron, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 825 days.

This patent is subject to a terminal disclaimer.

(21) Appl. No.: 17/554,055

(22) Filed: Dec. 17, 2021

(65) Prior Publication Data

US 2022/0104952 A1    Apr. 7, 2022

Related U.S. Application Data (63) Continuation of application No. 16/529,198, filed on Aug. 1, 2019, now Pat. No. 11,207,197.

(51) Int. Cl.
    A61F 2/46    (2006.01)
    A61F 2/30    (2006.01)
    A61F 2/36    (2006.01)

(52) U.S. Cl.
    CPC .......... *A61F 2/4637* (2013.01); *A61F 2/4607* (2013.01); *A61F 2002/30069* (2013.01);
    (Continued)

(58) Field of Classification Search
    None
    See application file for complete search history.

(56) References Cited

U.S. PATENT DOCUMENTS

| | | | |
|---|---|---|---|
| 1,435,278 | A | 11/1922 | Campbell |
| 1,595,658 | A | 8/1926 | Heinrich |
| (Continued) | | | |

FOREIGN PATENT DOCUMENTS

| | | |
|---|---|---|
| CN | 1513423 A | 7/2004 |
| CN | 103356288 | 10/2013 |
| (Continued) | | |

OTHER PUBLICATIONS

International Search Report for International Application No. PCT/IB2020/056712, Oct. 19, 2020, 8 pages.

*Primary Examiner* — Brian A Dukert
*Assistant Examiner* — Melissa A Hoban
(74) *Attorney, Agent, or Firm* — Barnes & Thornburg LLP (57) ABSTRACT An orthopaedic surgical instrument includes an assembly collar having a cavity extending between a superior opening and an inferior opening. The cavity is sized to receive a tapered trunnion of an implanted femoral stem. A bore extends between an inferior end and a superior end of the assembly collar and is configured to align with an implant bore formed in the implanted femoral stem. The bore and the implant bore are configured to receive a fastener to secure the assembly collar to the implanted femoral stem. A method of utilizing the orthopaedic surgical instrument is also contemplated.

14 Claims, 5 Drawing Sheets

(52) U.S. Cl.
CPC ............... *A61F 2002/30405* (2013.01); *A61F 2002/365* (2013.01); *A61F 2002/4638* (2013.01); *A61F 2002/4681* (2013.01)

(56) References Cited

U.S. PATENT DOCUMENTS

| | | | |
|---|---|---|---|
| 1,794,494 | A | 3/1931 | Noble |
| 2,190,585 | A | 2/1940 | Rhinevault |
| 2,408,801 | A | 10/1946 | Miller |
| 2,863,477 | A | 12/1958 | Sagerty |
| 3,102,536 | A | 9/1963 | Rose et al. |
| 3,801,989 | A | 4/1974 | McKee |
| 4,284,080 | A | 8/1981 | Rehder |
| 4,705,520 | A | 11/1987 | Ahrens |
| 4,795,472 | A | 1/1989 | Crowninshield et al. |
| 4,865,609 | A | 9/1989 | Roche |
| 4,921,500 | A | 5/1990 | Averill et al. |
| 4,922,898 | A | 5/1990 | Dunn |
| 4,936,863 | A | 6/1990 | Hofmann |
| 5,133,765 | A | 7/1992 | Cuilleron |
| 5,171,324 | A | 12/1992 | Campana et al. |
| 5,342,362 | A | 8/1994 | Kenyon et al. |
| 5,514,136 | A | 5/1996 | Richelsoph |
| 5,626,584 | A | 5/1997 | Young |
| 5,849,015 | A | 12/1998 | Haywood et al. |
| 5,966,792 | A | 10/1999 | James |
| 6,113,605 | A | 9/2000 | Storer |
| 6,224,605 | B1 | 5/2001 | Anderson et al. |
| 6,629,982 | B2 | 10/2003 | Day et al. |
| 6,827,741 | B2 | 12/2004 | Reeder |
| 7,497,875 | B1 | 3/2009 | Zweymller |
| 7,661,162 | B2 | 2/2010 | Soerensen et al. |
| 7,699,847 | B2 | 4/2010 | Sheldon et al. |
| 8,070,822 | B1 | 12/2011 | Iversen |
| 8,152,855 | B2 | 4/2012 | Tulkis et al. |
| 8,518,050 | B2 | 8/2013 | Mccleary et al. |
| 8,533,921 | B2 | 9/2013 | Eisinger et al. |
| 9,833,339 | B2 | 12/2017 | Froidevaux et al. |
| 2003/0065398 | A1 | 5/2003 | Cueille et al. |
| 2003/0229357 | A1* | 12/2003 | Dye ..................... A61F 2/4637 606/99 |
| 2004/0236341 | A1 | 11/2004 | Petersen |
| 2004/0267373 | A1 | 12/2004 | Dwyer et al. |
| 2007/0162038 | A1 | 7/2007 | Tuke |
| 2008/0119944 | A1 | 5/2008 | Bruce et al. |
| 2009/0281632 | A1 | 11/2009 | Naidu |
| 2011/0009976 | A1 | 1/2011 | Cruchet |
| 2012/0253469 | A1 | 10/2012 | Collins |
| 2012/0259338 | A1 | 10/2012 | Carr et al. |
| 2016/0206430 | A1 | 7/2016 | Grostefon et al. |
| 2016/0206443 | A1 | 7/2016 | Brooks et al. |
| 2016/0206444 | A1 | 7/2016 | Schmalzried |
| 2016/0206445 | A1 | 7/2016 | Gheevarughese et al. |
| 2019/0192300 | A1 | 6/2019 | Brooks et al. |

FOREIGN PATENT DOCUMENTS

| | | |
|---|---|---|
| CN | 103813764 A | 5/2014 |
| DE | 29824993 U1 | 12/2003 |
| DE | 202012102017 U1 | 9/2013 |
| EP | 200672 A1 | 11/1986 |
| EP | 0940128 A2 | 9/1999 |
| EP | 1080701 A2 | 3/2001 |
| EP | 1437107 A1 | 7/2004 |
| EP | 1776937 A1 | 4/2007 |
| JP | 3165299 U | 1/2011 |
| JP | 2014516613 A | 7/2014 |
| WO | 2000059410 | 10/2000 |
| WO | 2016115330 A1 | 7/2016 |
| WO | 2016115359 A1 | 7/2016 |
| WO | 2016115364 A1 | 7/2016 |
| WO | 2016115365 A1 | 7/2016 |

* cited by examiner

ORTHOPAEDIC SURGICAL INSTRUMENT FOR TOTAL HIP ARTHROPLASTY AND ASSOCIATED ORTHOPAEDIC SURGICAL METHOD OF USE

This application is a continuation of U.S. patent application Ser. No. 16/529,198, now U.S. Pat. No. 11,207,197, which was filed on Aug. 1, 2019, the entirety of which is hereby incorporated by reference.

TECHNICAL FIELD

The present disclosure relates generally to orthopaedic instruments, and particularly to orthopaedic instruments for use in hip replacement surgery.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is received in the medullary canal of the patient's femur and a spherically-shaped head component that bears against the patient's acetabulum or a prosthetic replacement acetabular cup.

SUMMARY

According to an aspect of the disclosed embodiments, an orthopaedic surgical instrument assembly for use during assembly of a femoral head component to an implanted femoral stem component during an orthopaedic hip replacement procedure may include an assembly collar that may have a cavity extending between a superior opening in a superior end thereof an inferior opening in an inferior end thereof. The cavity may be configured such that, when the assembly collar is secured to the implanted femoral stem component, a tapered trunnion of a femoral implant may extend into the cavity through the inferior opening thereof. The cavity may be configured such that, when the assembly collar is secured to the implanted femoral stem component, the femoral head component may be received in the superior opening of the cavity. The assembly collar may also include a bore extending from the superior end of the assembly collar to the inferior end of the assembly collar. The bore may be configured to align with an implant bore formed in the implanted femoral stem component when the assembly collar is secured to the implanted femoral stem component. A fastener may be positioned in the bore. The fastener may be configured to be received into the implant bore formed in the implanted femoral stem component when the assembly collar is secured to the implanted femoral stem component.

In some embodiments, the fastener may be a threaded bolt that is configured to threadingly engage a set of threads formed in the implant bore when the assembly collar is secured to the implanted femoral stem component. An outer surface of the femoral head component may be accessible by an impaction instrument through the superior opening of the cavity of the assembly collar when the femoral head component is positioned within the cavity.

In some embodiments, an impaction guide may be coupled to the assembly collar. The impaction guide may be configured to align an impaction instrument along a longitudinal axis of the tapered trunnion. The impaction guide may include a guide slot. A longitudinal axis of the guide slot may be aligned with the longitudinal axis of the tapered trunnion. The guide slot may be configured to receive a shaft of the impaction instrument therein. The impaction guide may include a number of tabs. A retainer may be secured to the tabs to retain the shaft of the impaction instrument when the shaft of the impaction instrument is positioned in the guide slot. The retainer may be an elastic band. A first end of a shaft may be secured to the assembly collar. A second end of the shaft may be secured to the impaction guide.

According to another aspect of the disclosed embodiments, an orthopaedic surgical instrument assembly for use during assembly of an orthopaedic component to an implanted component that is implanted in a patient bone may include an assembly collar that may have a cavity extending between a superior opening in a superior end thereof an inferior opening in an inferior end thereof. The cavity may be configured such that, when the assembly collar is secured to the implanted component, an end of the implanted component may extend into the cavity through the inferior opening thereof. The cavity may be configured such that, when the assembly collar is secured to the implanted component, the orthopaedic component may be received in the superior opening of the cavity. The assembly collar may also include a bore extending from the superior end of the assembly collar to the inferior end of the assembly collar. The bore may be configured to align with an implant bore formed in the implanted component when the assembly collar is secured to the implanted component. A fastener may be positioned in the bore. The fastener may be configured to be received into the implant bore formed in the implanted component when the assembly collar is secured to the implanted component.

In some embodiments, the fastener may be a threaded bolt that is configured to threadingly engage a set of threads formed in the implant bore when the assembly collar is secured to the implanted component. An outer surface of the orthopaedic component may be accessible by an impaction instrument through the superior opening of the cavity of the assembly collar when the orthopaedic component is positioned within the cavity.

In some embodiments, an impaction guide may be coupled to the assembly collar. The impaction guide may be configured to align an impaction instrument along a longitudinal axis of the end of the implanted component. The impaction guide may include a guide slot. A longitudinal axis of the guide slot may be aligned with the longitudinal axis of the end of the implanted component. The guide slot may be configured to receive a shaft of the impaction instrument therein. The impaction guide may include a number of tabs. A retainer may be secured to the tabs to retain the shaft of the impaction instrument when the shaft of the impaction instrument is positioned in the guide slot. The retainer may be an elastic band. A first end of a shaft may be secured to the assembly collar. A second end of the shaft may secured to the impaction guide.

According to yet another aspect of the disclosed embodiments, a method of assembling a femoral head component to an implanted femoral stem component during an orthopaedic hip replacement procedure may include positioning an assembly collar on the implanted femoral stem so that a tapered trunnion of the implanted femoral stem extends into a cavity extending between a superior opening and an inferior opening of the assembly collar. The method may also include positioning a femoral head component on the tapered trunnion so that the femoral head component is positioned within the cavity and an outer surface of the femoral head component is accessible through the superior opening. The method may also include striking the femoral head component with an impaction instrument that is extended through the superior opening and contacting the outer surface of the femoral head component.

In some embodiments, the method may include securing the assembly collar to the implanted femoral stem with a fastener that extends through a bore in the assembly collar and an implant bore in the implanted femoral stem. The method may also include coupling an impaction guide to the assembly collar. The method may also include aligning the impaction instrument along a longitudinal axis of the tapered trunnion with the impaction guide. The method may also include aligning a longitudinal axis of a slot of the impaction guide with the longitudinal axis of the tapered trunnion. The method may also include positioning a shaft of the impaction instrument within the slot.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
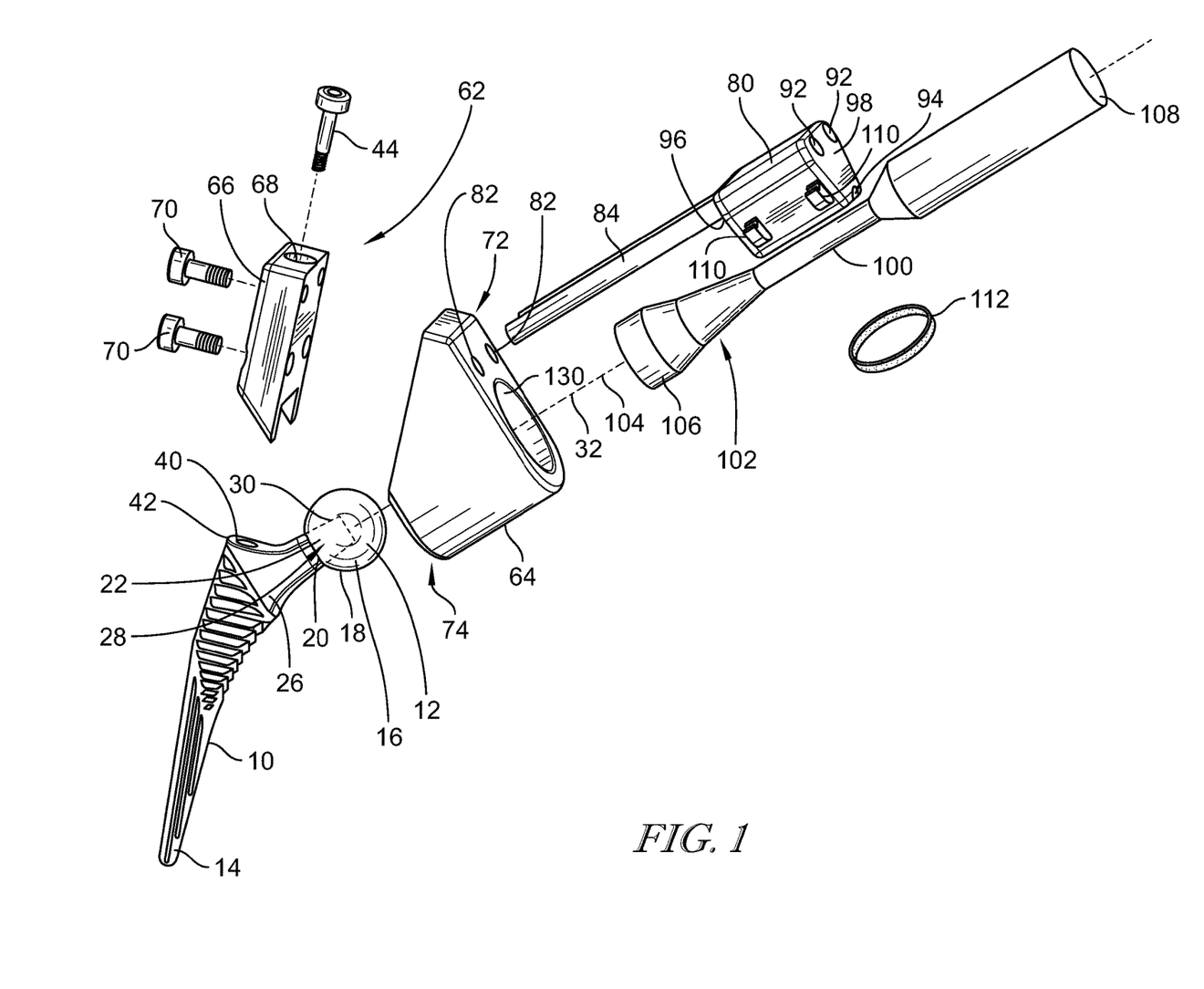
FIG. 1 is an exploded view of an orthopaedic surgical instrument assembly for use in an orthopaedic hip replacement procedure.

Referring to FIG. 1, an orthopaedic prosthesis is illustratively embodied as a femoral orthopaedic implant 10 of a hip prosthesis. The femoral orthopaedic implant 10 (hereinafter implant 10) includes a head component 12 and an elongated stem component 14 that is configured to be implanted into an intramedullary canal of a patient's surgically-prepared femur (not shown). The head component 12 includes a spherical outer surface 16 configured to engage a patient's natural acetabulum (not shown) or a prosthetic acetabular cup implanted into the patient's pelvic bone. The head component 12 also includes a distal surface 18 having an opening 20 defined therein. An inner wall 30 extends inwardly from the opening 20 to define a tapered bore 22 in the head component 12.

The stem component 14 of the implant 10 includes a neck 26 configured to be coupled to the head component 12. In the illustrative embodiment, the neck 26 includes a tapered trunnion 28 that extends along a longitudinal axis 32. The tapered bore 22 of the head component 12 is taper fit onto the tapered trunnion 28 so as to secure the head component 12 to the stem component 14.

The neck 26 also includes a bore 40 extending from a bore opening 42 and into the neck 26. The bore 40 is configured to receive a fastener 44 to secure other components to the implant 10. In the illustrative embodiment, the fastener 44 is a bolt and the bore 40 is threaded and configured to engage threads on the fastener 44.

The orthopaedic surgical instrument disclosed herein illustratively includes an assembly collar 60 configured to be secured to the neck 26 of the implant 10. The assembly collar 60 includes a body 62 formed from a main body 64 and an attachment body 66. The attachment body 66 is coupled to the main body 64 with fasteners 70 to secure the assembly collar 60 around the tapered trunnion 28 and head component 12 of the implant 10. The attachment body 66 includes a bore 68 that aligns with the bore 40 of the femoral implant 10 when the assembly collar 60 is secured to the implant 10. The bore 68 extends from a superior end 72 to an inferior end 74 of the assembly collar 60. The fastener 44 is received through the bore 68 and secured to the threads of the implant bore 40 to secure the assembly collar 60 to the implant 10.

An impaction guide 80 extends from the assembly collar's main body 64. The main body 64 includes a pair of openings 82 that each receive a respective shaft 84 of the impaction guide 80. The shafts 84 extend outwardly from the main body 64 parallel to the longitudinal axis 32 of the femoral implant's tapered trunnion 28. The impaction guide 80 is secured to the shafts 84. That is, each shaft 84 is received in a respective bore 92 of the impaction guide 80. The impaction guide 80 may be configured to move along the shafts 84, in some embodiments. In other embodiments, the impaction guide 80 is frictionally secured to the shafts 84.

The impaction guide 80 includes a slot 94 extending from a proximal end 96 of the impaction guide 80 to a distal end 98 of the impaction guide 80. The slot 94 extends parallel to the longitudinal axis 32 of the tapered trunnion 28 of the femoral implant 10 when the impaction guide 80 is secured thereto. A shaft 100 of an impaction instrument 102 is configured to be positioned in the slot 94 so that a longitudinal axis 104 of the shaft 100 extends collinear with the longitudinal axis 32 of the femoral implant's tapered trunnion 28. The impaction instrument 102 includes an impaction head 106 that engages the head component 12, and an impaction end 108 that is configured to be struck with a hammer, mallet, or the like. Tabs 110 on the impaction guide 80 retain a retainer 112 to secure the impaction instrument 102 to the impaction guide 80. For example, the retainer 112 may be an elastic band that wraps around the shaft 100 of the impaction instrument 102.

The assembly collar 60 has a mass that increases the mass of the implant 10 when the assembly collar 60 is secured to the implant 10. It has been shown that the higher the mass of an object being impacted, the higher the impact force. That is, by adding mass to the implant 10, an inertia of the implant increases when the implant 10 is struck with the impaction instrument 102. Rigidly connecting the assembly collar 60 to the implant 10 increases the implant's mass/inertia, which leads to increased assembly force when the head component 12 is struck with the impaction instrument 102 and an increased femoral head component pull-off force after the head component 12 is secured to the tapered trunnion 28.

Figure 2:
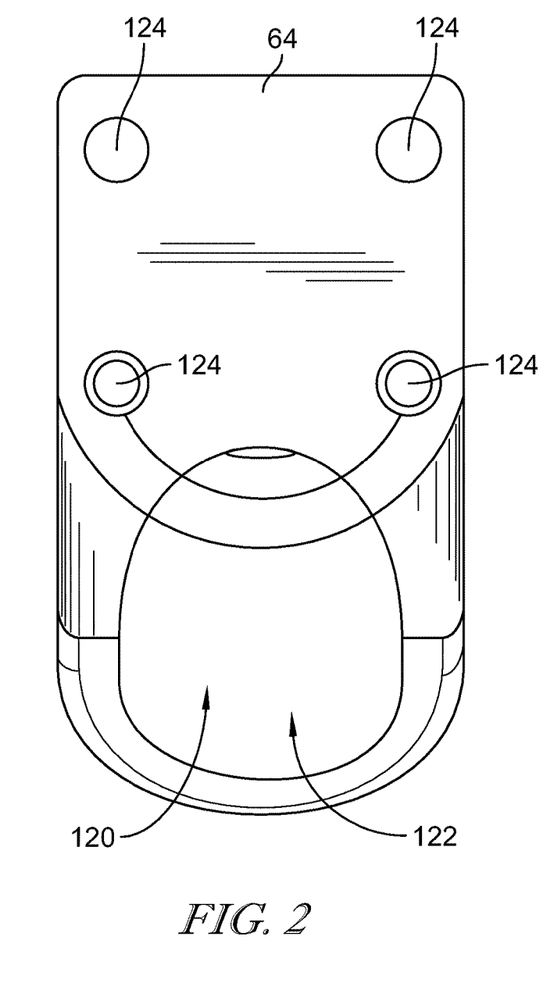
FIG. 2 is a rear elevation view of the main body of the assembly collar of the instrument assembly of FIG. 1.
Figure 3:
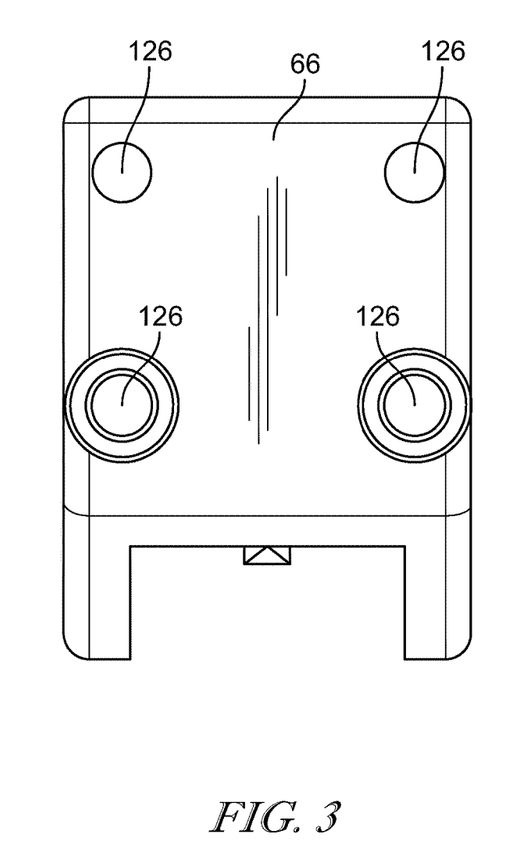
FIG. 3 is a rear elevation view of the attachment body of the assembly collar of the instrument assembly of FIG. 1.

Referring now to FIG. 2, the main body 64 of the assembly collar 60 includes a cavity 120 extending from an inferior opening 122. As described in more detail below, the cavity 120 extends entirely through the main body 64. The main body 64 also includes bores 124 that are configured to receive the fasteners 70. The bores 124 are configured to be aligned with bores 126 formed in the attachment body 66, as shown in FIG. 3. The fasteners 70 are extended through the bores 126 of the attachment body 66 and are secured within the bores 124 of the main body 64. In some embodiments, the bores 124 of the main body 64 are threaded and configured to receive threaded fasteners 70.

Figure 4:
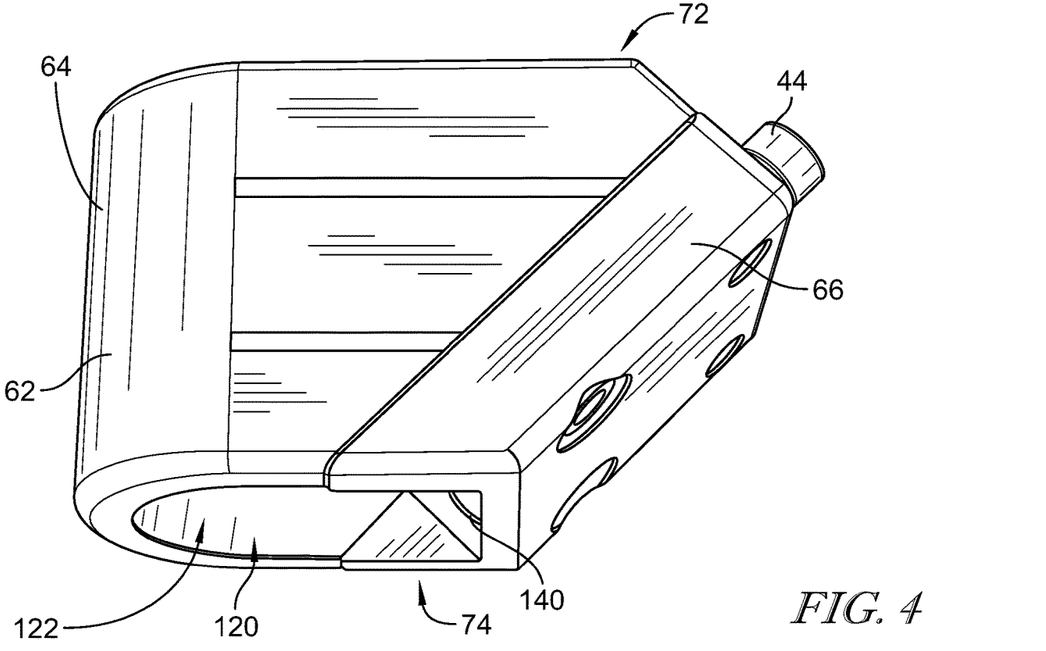
FIG. 4 is a side perspective view showing the attachment body coupled to the main body to form the body of the assembly collar shown in FIG. 1.
Figure 5:
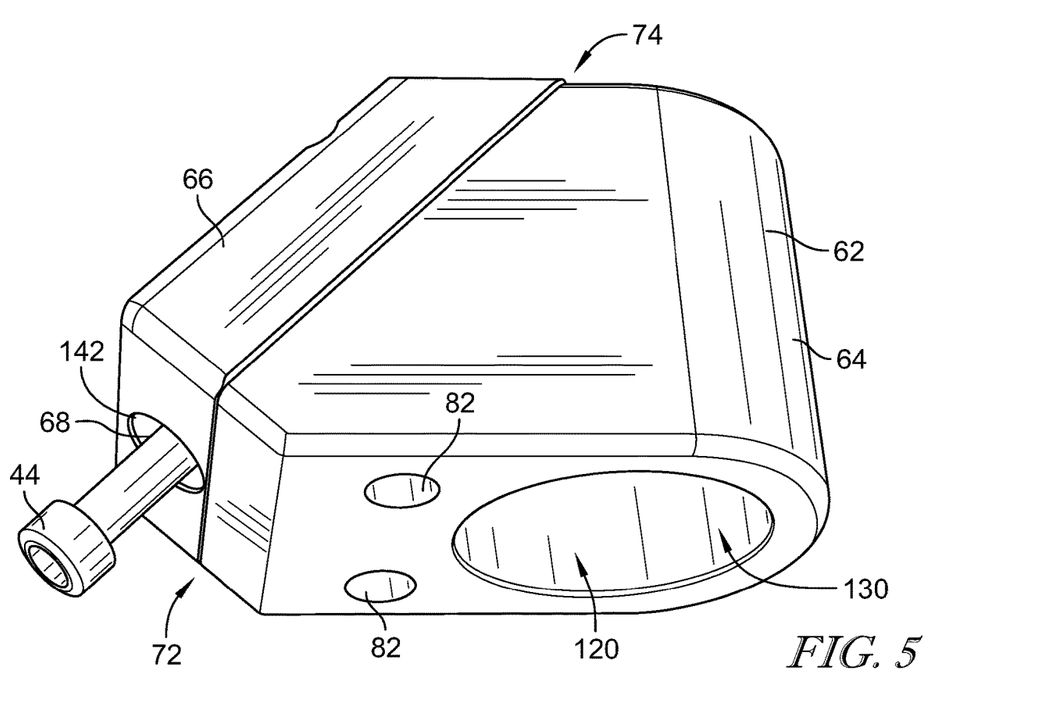
FIG. 5 is another side perspective view showing the attachment body coupled to the main body to form the body of the assembly collar shown in FIG. 1.

FIGS. 4 and 5 illustrate the attachment body 66 coupled to the main body 64 to form the body 62 of the assembly collar 60. As shown in FIG. 4, the inferior opening 122 is partially formed in the main body 64 and partially formed in the attachment body 66. The cavity 120 extends from the inferior opening 122 to a superior opening 130, shown in FIG. 5. Additionally, the bore 68 extends through the attachment body 66 from a bore opening 140 (shown in FIG. 4) to a bore opening 142 (shown in FIG. 5). As set forth above, the bore 68 is configured to receive the fastener 44 to secure the body 62 to the implant 10.

Figure 6:
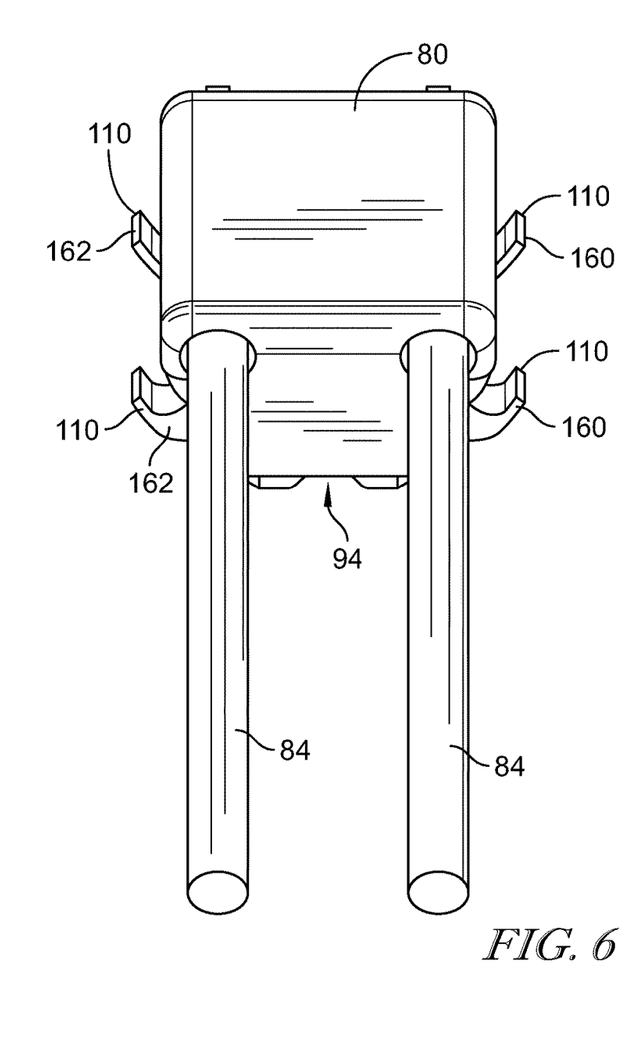
FIG. 6 is a rear perspective view of the alignment guide of the instrument assembly of FIG. 1.

FIG. 5 also illustrates the openings 82 in the main body 64. The openings 82 are configured to receive the shafts 84 of the impaction guide 80 (shown in FIGS. 6 and 7). The shafts 84 are configured to extend from the body 62 so that the impaction guide 80 of the impaction guide 80 can be positioned a distance from the assembly collar 60. In other embodiments, the impaction guide 80 may only include a single shaft 84. The assembly collar 60 is configured to be utilized with or without the impaction guide 80. For example, when the assembly collar 60 is not being used with the impaction guide 80, the shafts 84 are not inserted into the openings 82 and the impaction instrument 102 is manually aligned by a surgeon. If the impaction guide 80 is to be used, the shafts 84 can be inserted into the openings 82 so that impaction guide 80 extends from the assembly collar 60. It should be noted that other components, other than the shafts 84, may be utilized to position the impaction guide 80 relative to the assembly collar 60.

Figure 7:
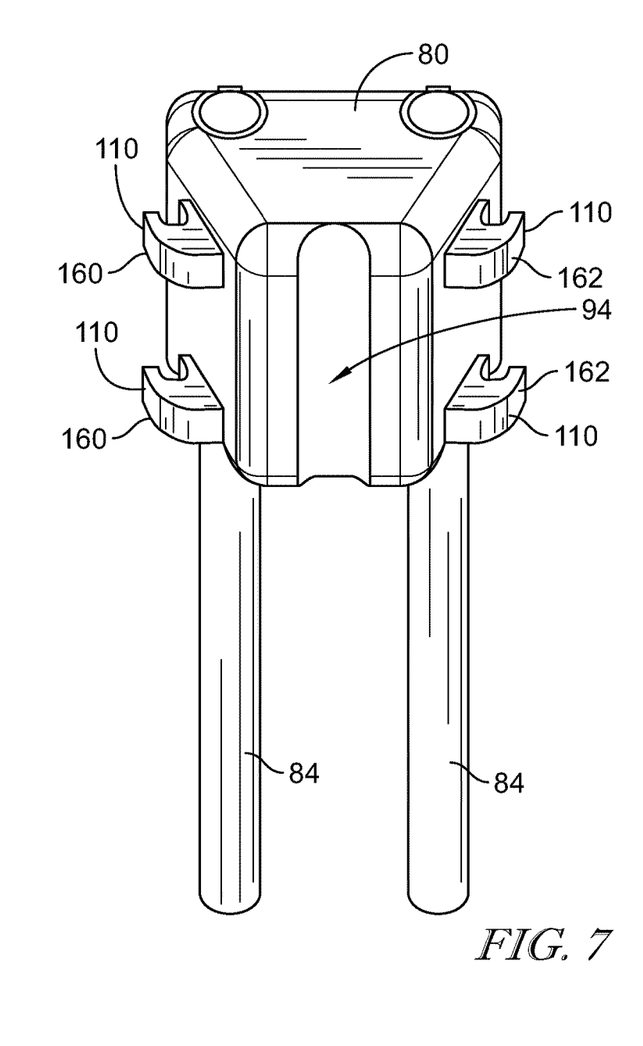
FIG. 7 is a front perspective view of the alignment guide of the instrument assembly of FIG. 1.

The impaction guide 80 is positioned so that the slot 94 aligns parallel to the longitudinal axis 32 of the femoral implant's tapered trunnion 28. When the shaft 100 of the impaction instrument 102 is positioned within the slot 94, the longitudinal axis 104 of the shaft 100 is positioned collinear with the longitudinal axis 32 of the tapered trunnion 28. As shown in FIG. 7, the tabs 110 are positioned on each side of the slot 94. Particularly, the impaction guide 80 includes two pairs of tabs 110. Each pair of tabs 110 includes a left tab 160 and a right tab 162. The retainer 112 extends from a left tab 160 to a right tab 162 across the slot 94. The impaction guide 80 may utilize a retainer 112 in each pair of tabs 110 or only in one pair of tabs 110 to stabilize the impaction instrument 102 in the slot 94. In some embodiments, the impaction instrument 102 may be stabilized manually without any retainer 112.

Figure 8:
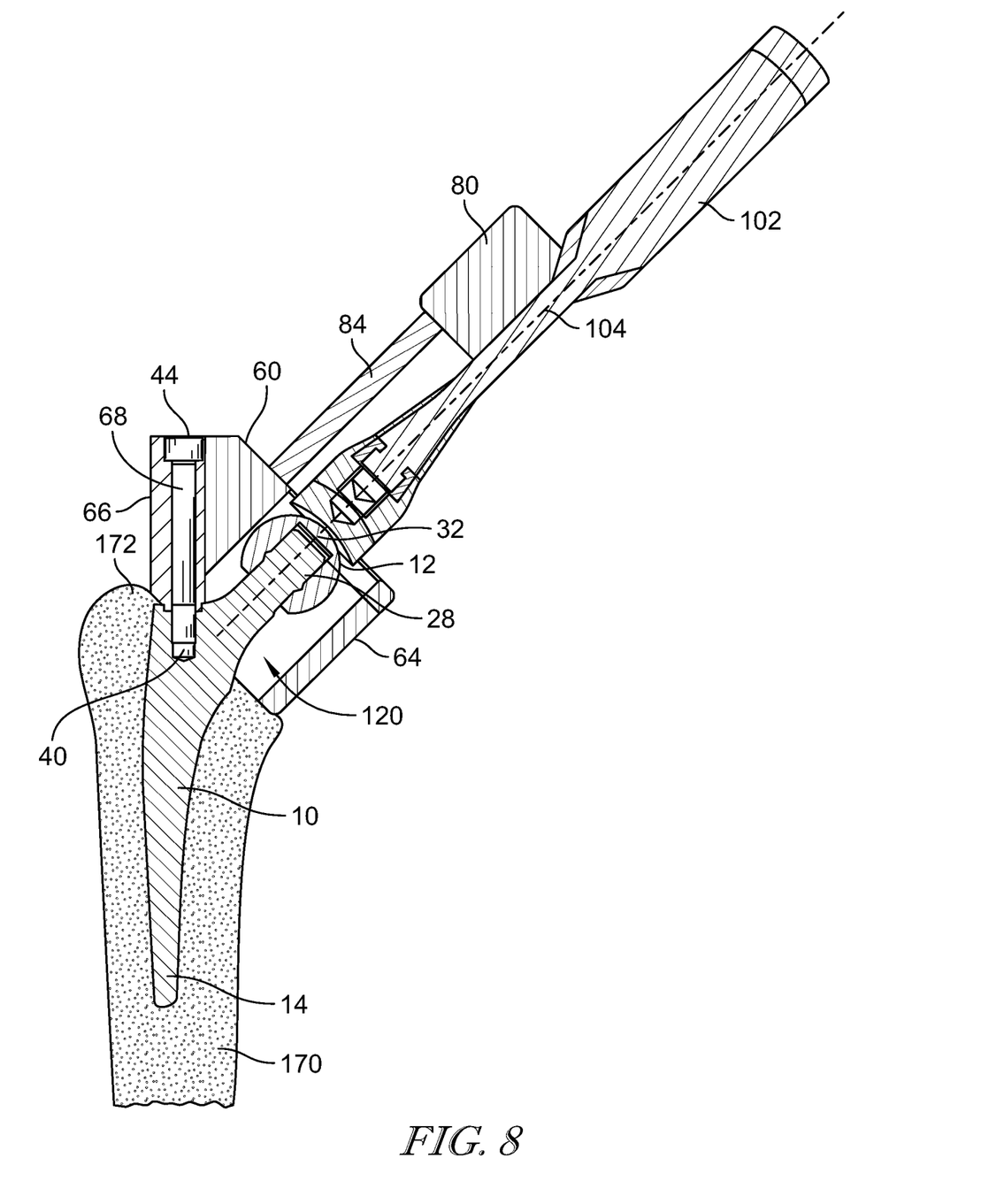
FIG. 8 is a side cross-sectional view of the orthopaedic surgical instrument secured to the femoral implant.

Referring now to FIG. 8, during a surgical procedure to replace a patient's hip, the stem component 14 of the implant 10 is implanted into the intramedullary canal of a patient's surgically-prepared femur 170. The tapered trunnion 28 of the implant 10 extends outward from a proximal end 172 of the femur 170. The head component 12 is positioned on the tapered trunnion 28 so as to be secured to the tapered trunnion 28 with the impaction instrument 102.

The assembly collar 60 is then assembled around the head component 12 and the tapered trunnion 28. That is, the attachment body 66 is secured to the main body 64 with the fasteners 70 so that the head component 12 and the tapered trunnion 28 are positioned within the cavity 120. The collar assembly 60 is secured to the implant 10 by extending the fastener 44 through the bore 68 of the assembly collar 60 and securing the fastener 44 into the bore 40 of the implant 10. The assembly collar 60 may then be utilized without the impaction guide 80 to secure the head component 12 to the tapered trunnion 28 by placing the impaction instrument 102 through the superior opening 130 and on an outer surface of the head component 12 and striking the impaction instrument 102 with a hammer, mallet, or the like. As set forth above, and described below, the assembly collar 60 increases the inertia of the implant 10 when the impaction instrument 102 is struck, thereby increasing a force with which the head component 12 is secured to the tapered trunnion 28.

If the surgeon chooses to have assistance in aligning the impaction instrument 102 with the longitudinal axis 32 of the tapered trunnion 28, the impaction guide 80 may be secured to the assembly collar 60. By extending the impaction guide 80 from the assembly collar 60, the longitudinal axis 104 of the shaft 100 of the impaction guide 102 is aligned collinearly with the longitudinal axis 32 of the tapered trunnion 28. Accordingly, the impact of the impaction instrument 102 may be directed along the longitudinal axis 32 of the tapered trunnion 28 to secure the head component 12 on the tapered trunnion 28.

In a test of the assembly collar 60, two cement-less stems, size 8, were assembled with 28 mm femoral heads. A first stem and femoral head pair were assembled without the assembly collar 60. A second stem and femoral head pair were assembled using an assembly collar 60 weighing 670 g. The stems were implanted in 10 pcf foam and a 2 lb weight was dropped on each pair from a 10 inch height.

The test resulted in a 58% increase in the average pull-off force for the second pair. Specifically, the average pull-off force for the first pair was approximately 312 lbf, and the average pull-off force of the second pair was approximately 493 lbf. The assembly collar 60 facilitated increasing femoral head fixation strength, thereby leading to a reduced micromotion and a reduced fretting corrosion with the same impaction.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of performing an orthopaedic hip replacement procedure, the method comprising:
   implanting a femoral stem component into a proximal end of a patient's femur,
   positioning a femoral head component on a tapered trunnion of the implanted femoral stem,
   positioning an assembly collar on the implanted femoral stem such that (i) the tapered trunnion of the implanted femoral stem extends into a cavity extending between a superior opening and an inferior opening of the assembly collar, and (ii) the femoral head component is positioned within the cavity and an outer surface of the femoral head component is accessible through the superior opening,
   striking the femoral head component with an impaction instrument that is extended through the superior opening and contacting the outer surface of the femoral head component,
   coupling an impaction guide to the assembly collar, and
   aligning the impaction instrument along a longitudinal axis of the tapered trunnion with the impaction guide.

2. The method of claim 1, further comprising securing the assembly collar to the implanted femoral stem with a fastener that extends through a bore in the assembly collar and an implant bore in the implanted femoral stem.

3. The method of claim 1, further comprising:
   aligning a longitudinal axis of a slot of the impaction guide with the longitudinal axis of the tapered trunnion, and
   positioning a shaft of the impaction instrument within the slot.

4. The method of claim 3, wherein:
   the impaction guide comprises a number of tabs,
   positioning the shaft of the impaction instrument within the slot comprises securing a retainer to the tabs to retain the shaft of the impaction instrument in the slot.

5. The method of claim 1, further comprising removing the assembly collar from the implanted femoral stem after striking the femoral head component.

6. A method of performing an orthopaedic hip replacement procedure, the method comprising:
   implanting a femoral stem component into a proximal end of a patient's femur,
   positioning a femoral head component on a tapered trunnion of the implanted femoral stem,
   positioning an assembly collar on the implanted femoral stem such that (i) the tapered trunnion of the implanted femoral stem extends into a cavity extending between a superior opening and an inferior opening of the assembly collar, and (ii) an outer surface of the femoral head component is accessible through the superior opening,
   striking the femoral head component with an impaction instrument that is extended through the superior opening and contacting the outer surface of the femoral head component, and
   securing the assembly collar to the implanted femoral stem with a fastener that extends through a bore in the assembly collar and an implant bore in the implanted femoral stem.

7. The method of claim 6, further comprising:
   coupling an impaction guide to the assembly collar, and
   aligning the impaction instrument along a longitudinal axis of the tapered trunnion with the impaction guide.

8. The method of claim 7, further comprising:
   aligning a longitudinal axis of a slot of the impaction guide with the longitudinal axis of the tapered trunnion, and
   positioning a shaft of the impaction instrument within the slot.

9. The method of claim 8, wherein:
   the impaction guide comprises a number of tabs,
   positioning the shaft of the impaction instrument within the slot comprises securing a retainer to the tabs to retain the shaft of the impaction instrument in the slot.

10. The method of claim 6, further comprising removing the assembly collar from the implanted femoral stem after striking the femoral head component.

11. A method of performing an orthopaedic hip replacement procedure, the method comprising:
    implanting a femoral stem component into a proximal end of a patient's femur,
    positioning a femoral head component on a tapered trunnion of the implanted femoral stem,
    positioning an assembly collar on the implanted femoral stem such that (i) the tapered trunnion of the implanted femoral stem extends into a cavity extending between a superior opening and an inferior opening of the assembly collar, and (ii) an outer surface of the femoral head component is accessible through the superior opening,
    striking the femoral head component with an impaction instrument that is extended through the superior opening and contacting the outer surface of the femoral head component,
    coupling an impaction guide to the assembly collar, and
    aligning the impaction instrument along a longitudinal axis of the tapered trunnion with the impaction guide.

12. The method of claim 11, further comprising:
    aligning a longitudinal axis of a slot of the impaction guide with the longitudinal axis of the tapered trunnion, and
    positioning a shaft of the impaction instrument within the slot.

13. The method of claim 12, wherein:
    the impaction guide comprises a number of tabs,
    positioning the shaft of the impaction instrument within the slot comprises securing a retainer to the tabs to retain the shaft of the impaction instrument in the slot.

14. The method of claim 11, further comprising removing the assembly collar from the implanted femoral stem after striking the femoral head component.

* * * * *